United States Patent
Chang

(12) 
(10) Patent No.: US 6,723,650 B1
(45) Date of Patent: Apr. 20, 2004

(54) TEM SAMPLE PREPARATION USING TRANSPARENT DEFECT PROTECTIVE COATING

(75) Inventor: Chieh-Fei Chang, Kaohsiung (TW)

(73) Assignee: Taiwan Semiconductor Manufacturing Co., Ltd., Hsin Chu (TW)

( * ) Notice: Subject to any disclaimer, the term of this patent is extended or adjusted under 35 U.S.C. 154(b) by 0 days.

(21) Appl. No.: 10/407,083

(22) Filed: Apr. 3, 2003

(51) Int. Cl.[7] .................................................. B44C 1/22
(52) U.S. Cl. ...................... 438/700; 216/59; 216/60; 216/84; 216/85; 216/37
(58) Field of Search ................ 438/11, 14, 15, 438/16, 17, 18, 700, FOR 101, FOR 102, FOR 142; 257/48, E23.179, E21.524, E21.529; 216/37, 59, 60, 84, 85

(56) References Cited

U.S. PATENT DOCUMENTS

2003/0150836 A1 * 8/2003 Tsung et al. .................. 216/67

* cited by examiner

Primary Examiner—George Fourson
Assistant Examiner—Julio J. Maldonado
(74) Attorney, Agent, or Firm—Tung & Associates

(57) ABSTRACT

A technique for preparing a TEM sample for imaging of a defect in a wafer section during the course of integrated circuit fabrication on semiconductor wafer substrates. The TEM sample preparation technique of the present invention includes cutting a first cross-section void in the wafer section to expose the defect, providing a substantially transparent material on the defect to protect the defect from cutting particles, depositing a cutting line on the wafer section adjacent to the first cross-section void, and cutting a second cross-section void along the cutting line to define a TEM sample having a selected thickness between the first and second cross-section voids and containing the defect.

8 Claims, 1 Drawing Sheet

TEM SAMPLE PREPARATION USING TRANSPARENT DEFECT PROTECTIVE COATING

FIELD OF THE INVENTION

The present invention relates to IC metrology and defect inspection techniques used in the inspection of defects in WIP (work-in-progress) wafers during the fabrication of semiconductor integrated circuits. More particularly, the present invention relates to preparation of a TEM (transmission electron microscopy) sample for IC defect inspection by providing a transparent protective coating over a defect on a sidewall in a first cross-section opening prior to milling a second cross-section opening in the sample on the opposite side of the defect, in order to prevent metal particle contamination of the defect.

BACKGROUND OF THE INVENTION

The fabrication of various solid state devices requires the use of planar substrates, or semiconductor wafers, on which integrated circuits are fabricated. The final number, or yield, of functional integrated circuits on a wafer at the end of the IC fabrication process is of utmost importance to semiconductor manufacturers, and increasing the yield of circuits on the wafer is the main goal of semiconductor fabrication. After packaging, the circuits on the wafers are tested, wherein non-functional dies are marked using an inking process and the functional dies on the wafer are separated and sold. IC fabricators increase the yield of dies on a wafer by exploiting economies of scale. Over 1000 dies may be formed on a single wafer which measures from six to twelve inches in diameter.

Various processing steps are used to fabricate integrated circuits on a semiconductor wafer. These steps include deposition of a conducting layer on the silicon wafer substrate; formation of a photoresist or other mask such as titanium oxide or silicon oxide, in the form of the desired metal interconnection pattern, using standard lithographic or photolithographic techniques; subjecting the wafer substrate to a dry etching process to remove the conducting layer from the areas not covered by the mask, thereby etching the conducting layer in the form of the masked pattern on the substrate; removing or stripping the mask layer from the substrate typically using reactive plasma and chlorine gas, thereby exposing the top surface of the conductive interconnect layer; and cooling and drying the wafer substrate by applying water and nitrogen gas to the wafer substrate.

The numerous processing steps outlined above are used to cumulatively apply multiple electrically conductive and insulative layers on the wafer and pattern the layers to form the circuits. The final yield of functional circuits on the wafer depends on proper application of each layer during the process steps. Proper application of those layers depends, in turn, on coating the material in a uniform spread over the surface of the wafer in an economical and efficient manner.

Throughout the IC fabrication process, the WIP wafers must be frequently tested to monitor the physical and electrical properties of the devices being fabricated thereon. Wafer testing is carried out on sample wafers using a measurement tool and equipment to analyze the data. These testing tools and equipment may use physical methods that allow ions, electrons and/or electromagnetic radiation to interact with the device features and then examine the secondary particles and/or radiations that are produced. The information obtained from the interaction of the particles and/or radiation with a region of interest in the device is then used to deduce the properties of the materials in the region of interest. The information reveals the presence of defects, which are characteristics of the wafer or results of the wafer fabrication process that cause nonconformance to the specified wafer requirements.

Some of the techniques widely used to inspect defects in wafers throughout IC fabrication include Scanning Electron Microscopy (SEM), Transmission Electron Microscopy (TEM), and Auger Electron Spectrometery (AES). The TEM method is particularly popular since transmission of electrons through a sample allows obtaining information via diffraction mechanisms which, in turn, provides information concerning longer-range order. TEM is a valuable tool used to quantify very small features on a wafer. For example, TEM can be used to image, on an atomic scale, silicon crystal point defects such as single dislocations that are introduced into an active junction by ion implant and lead to junction leakage. In TEM, a beam of electrons is transmitted through an ultra thin (about 10–100 nm thick) slice of the sample. Based on such factors as electron wavelength, accelerating voltage and specimen thickness, an image is formed and magnified on a screen with a resolution of about 2 angstroms. Unfortunately, sample preparation for TEM analysis is difficult and time-consuming since the thickness of the sample must not exceed about 100 nm to yield meaningful results.

Several techniques have been used to prepare TEM samples that do not exceed the typical 100 nm thickness limit for optimum imaging. Since the early 1990s, sample cross-sections have been prepared using a milling technique which is carried out by Focused Ion Beam (FIB) technology. The FIB technique uses an ion beam made of gallium ions that are focused through a set of lenses into a small spot on the wafer. At the point where they strike the wafer, the gallium ions are ejected into a vacuum, creating a small void, the shape and depth of which is precisely controlled, in the sample.

The FIB milling technique is illustrated in FIGS. 1 and 2. According to the FIB milling technique, a first cross-section void 16 is initially cut in the top surface 14 of a wafer section 10, adjacent to a defect 20 to be subsequently imaged using TEM, using a focused ion beam 24 ejected from an FIB apparatus 23. The defect 20 appears in a sidewall 18 of the first cross-section void 16. A metal cutting line 22 deposited on the top surface 14 serves as a guide along which the wafer section 10 is to be subsequently cut for preparation of the TEM sample 19 which contains the defect 20. The metal cutting line 22, which is typically platinum or tungsten, is deposited using any appropriate metal deposition method, such as by use of the FIB apparatus 23 using a low beam intensity.

As shown in FIG. 2, the focused ion beam 24 cuts the wafer section 10 along the metal cutting line 22 to form a second cross-section void 26, leaving the TEM sample 19 which contains the defect 20 separating the first cross-section void 16 and the second cross-section void 26. The focused ion beam 24 cuts the TEM sample 19 to a thickness of typically less than 100 nm. Finally, the TEM sample 19 is subjected to a transmission electron microscopy (TEM) technique in which electrons are transmitted through the TEM sample 19 for imaging of the defect 20. Based on such factors as electron wavelength, accelerating voltage and specimen thickness, an image of the defect 20 is formed and magnified on a screen (not shown) to reveal information such as the type and dimension of the defect 20. This information is used by IC manufacturing personnel to make corrective measures to the various process parameters likely to have caused the defect in an effort to ensure product performance and quality.

One of the drawbacks associated with the conventional FIB milling technique is that as the focused ion beam 24 cuts the wafer section 10 along the metal cutting line 22 to form the second cross-section void 26, metal particles frequently are dislodged from the metal cutting line 22 and deposited on the exposed defect 20 in the TEM sample 19. This adversely affects the quality and accuracy of the TEM image of the defect 20 that is generated during the subsequent TEM step. Accordingly, a technique is needed for protecting the defect from deposit of metal particles thereon during the milling operation in order to achieve a clear, accurate and high-quality TEM image of the defect.

Accordingly, an object of the present invention is to provide a technique for preserving the quality of a defect in a TEM sample during a sample-milling operation.

Another object of the present invention is to provide a technique for preventing the contamination of a defect in a TEM sample during a sample-milling operation.

Still another object of the present invention is to provide a technique for preventing metal particles from contaminating a defect in a TEM sample during a sample-milling operation.

Yet another object of the present invention is to provide a method for preserving the integrity and TEM imaging potential of a defect on a sidewall in a first cross-section void in a TEM sample, which method includes providing a substantially transparent material on the defect prior to cutting a second cross-section void in the sample to prevent the accumulation of metal particles on the defect.

Still another object of the present invention is to provide a method of preparing a TEM sample for imaging of a defect including providing a wafer section containing the defect, cutting a first cross-section void in the wafer section to expose the defect, providing a substantially transparent material on the defect, depositing a metal cutting line on the wafer section adjacent to the first cross-section void, and cutting a second cross-section void along the cutting line to define the TEM sample having a selected thickness between the voids and containing the defect.

A still further object of the present invention is to provide a TEM sample prepared by providing a wafer section containing a defect, cutting a first cross-section void in the wafer section to expose the defect, providing a substantially transparent material on the defect, depositing a metal cutting line on the wafer section adjacent to the first cross-section void, and cutting a second cross-section void along the cutting line to define the TEM sample having a selected thickness and containing the defect.

Another object of the present invention is to provide a sample for imaging a defect, including a wafer section; a first cross-section void provided in the wafer section; a second cross-section void provided in the wafer section adjacent to the first cross-section void; a TEM sample containing the defect separating the first cross-section void and the second cross-section void; and a substantially transparent material provided on the defect.

SUMMARY OF THE INVENTION

In accordance with these and other objects and advantages, the present invention is generally directed to a new and improved technique for preparing a TEM sample for imaging of a defect in a wafer section during the course of integrated circuit fabrication on semiconductor wafer substrates. The TEM sample preparation technique of the present invention includes cutting a first cross-section void in the wafer section to expose the defect, providing a substantially transparent material on the defect to protect the defect from cutting particles, depositing a typically metal cutting line on the wafer section adjacent to the first cross-section void, and cutting a second cross-section void along the metal cutting line to define a TEM sample having a selected thickness between the first and second cross-section voids and containing the defect.

The present invention is further directed to a TEM sample prepared by providing a wafer section containing a defect, cutting a first cross-section void in the wafer section to expose the defect, providing a substantially transparent material on the defect, depositing a metal cutting line on the wafer section adjacent to the first cross-section void, and cutting a second cross-section void along the cutting line to define the TEM sample having a selected thickness and containing the defect.

The present invention is further directed to a sample for imaging a defect, including a wafer section; a first cross-section void provided in the wafer section; a second cross-section void provided in the wafer section adjacent to the first cross-section void; a TEM sample containing the defect separating the first cross-section void and the second cross-section void; and a substantially transparent material provided on the defect.

The TEM sample typically has a thickness of less than about 100 nm, and may have a thickness of typically from about 10 nm to about 100 nm. In a typical embodiment, the substantially transparent material deposited on the defect is a clear epoxy material. The epoxy material may be a two-component epoxy material in which an "A" component is mixed with a "B" component to form the final transparent epoxy material.

BRIEF DESCRIPTION OF THE DRAWINGS

The invention will now be described, by way of example, with reference to the accompanying drawings, in which.

DESCRIPTION OF THE PREFERRED EMBODIMENTS

The present invention includes a new and improved method or technique for the preparation of a TEM (transmission electron microscopy) sample that contains a defect in a wafer section of a WIP (work-in-progress) semiconductor wafer substrate. The method includes providing a substantially clear or transparent coating material on a defect in a first cross-sectional void cut in the wafer section typically using a focused ion beam (FIB) technique. The coating material protects the defect from metal particles that are dislodged from a typically metal cutting line as a second cross-sectional void is cut in the wafer section along the cutting line to define the TEM sample between the voids. Consequently, the translucence of the TEM sample is enhanced for the subsequent TEM defect imaging step. This provides a defect image that is precise, accurate and high-quality in the metrology of defects during the semiconductor fabrication process.

The present invention further includes a TEM sample which is prepared by cutting a first cross-section void in a wafer section to expose a defect in a sidewall of the first cross-section void, providing a substantially clear or transparent material on the sidewall containing the defect, depositing a typically metal cutting line on the wafer section to guide in the focused ion beam (FIB) cutting of a second cross-section void in the wafer section, and cutting the second cross-section void in the wafer section to define the ultra thin TEM sample containing the defect between the voids.

The present invention still further includes a sample for imaging a defect in a WIP wafer, which sample includes a wafer section; a first cross-section void provided in the wafer section; a second cross-section void provided in the wafer section adjacent to the first cross-section void; a TEM sample containing the defect separating the first cross-section void and the second cross-section void; and a substantially transparent material provided on the defect.

Figure 1:
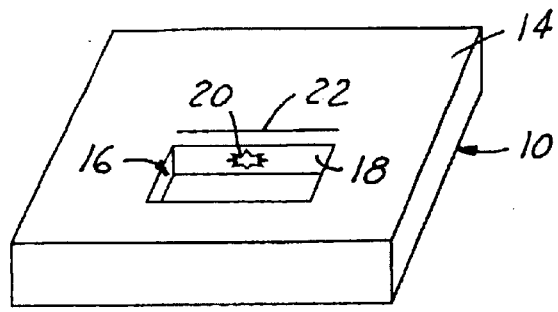
FIG. 1 is a perspective view of a wafer section containing a first cross-section void as a first step in conventional preparation of a TEM sample for imaging of a defect in the wafer section.
Figure 2:
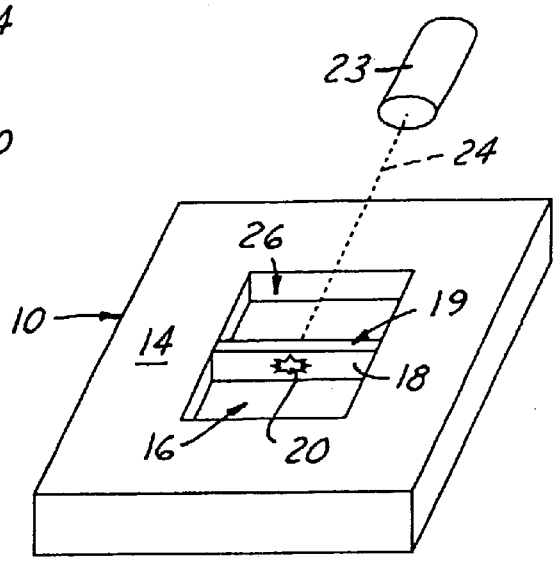
FIG. 2 is a perspective view of the wafer section of FIG. 1, more particularly illustrating cutting of a second cross-section void in the TEM sample as a second step in conventional preparation of a TEM sample for imaging of a defect in the wafer section.
Figure 3:
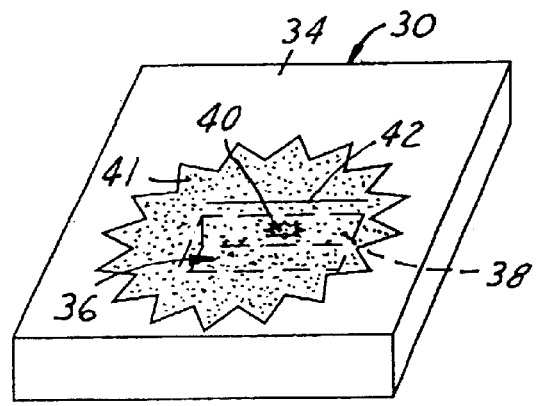
FIG. 3 is a perspective view of a wafer section containing a first cross-section void as a first step in preparation of a TEM sample for imaging of a defect in the wafer section in accordance with the present invention, with a transparent material coated on the defect.
Figure 4:
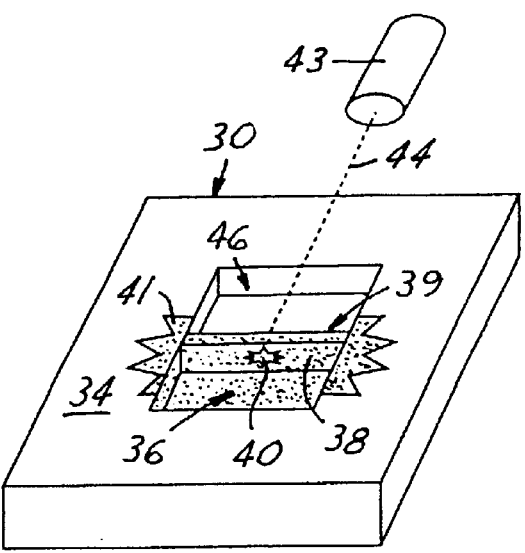
FIG. 4 is a perspective view of the wafer section of FIG. 3, more particularly illustrating cutting of a second cross-section void in the TEM sample as a second step in preparation of a TEM sample for imaging of a defect in the wafer section.
Figure 5:
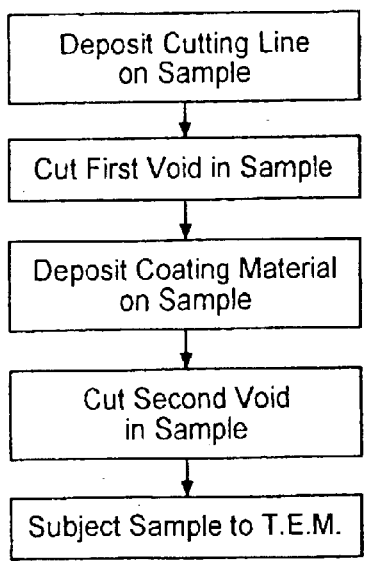
FIG. 5 is a flow diagram illustrating sequential steps in the preparation of a TEM sample according to the present invention.

Referring to FIGS. 3–5, a TEM sample 39 (FIG. 4) having a defect 40, which may be a particle defect or a CD (critical dimension) defect, for example, is prepared in a wafer section 30 in accordance with the present invention. The wafer section 30 is typically cut from a whole patterned wafer at a selected point during the semiconductor fabrication process. The TEM sample 39 is prepared and subjected to TEM (transmission electron microscopy), in which the type, number and characteristics of the defect 40 are analyzed in order to adopt corrective measures to the fabrication process to ensure optimum product quality and performance.

The successive steps of TEM sample preparation are outlined in FIG. 5. As a first step in the preparation of the TEM sample 39, a typically metal cutting line 42 is deposited on the top surface 34 of the wafer section 30, above the defect 40 to be imaged in a subsequent TEM step. The metal cutting line 42 may be deposited on the top surface 34 using any appropriate metal deposition method known by those skilled in the art. For example, the metal cutting line 42 may be deposited on the top surface 34 using an FIB apparatus 30, according to methods which are well-known by those skilled in the art. However, it is understood that materials other than metal may be deposited on the top surface 34 to define the cutting line 42.

After the cutting line 42 is deposited on the top surface 34 over the defect 40, a first cross-section void 36 is cut in the top surface 34 of the wafer section 30, along the cutting line 42, typically using a focused ion beam (FIB) 44 of gallium ions ejected from an FIB apparatus 43. The first cross-section void 36 includes a sidewall 38 that contains the defect 40. Next, a transparent coating material 41 is coated on the interior surfaces of the first cross-section void 36, including the sidewall 38 and the defect 40. The transparent coating material 41 is typically a clear, two-component epoxy which is prepared by mixing an "A" component with a "B" component to define the epoxy transparent coating material 41. However, it is understood that various other transparent materials known by those skilled in the art may be used instead.

After the transparent coating material 41 is provided on the sidewall 38 and defect 40, a second cross-section void 46 is cut in the top surface 34 of the wafer section 30, along the cutting line 42. This is typically accomplished by directing a focused ion beam 44 typically of gallium cations against the top surface 34 and along the cutting line 42. Accordingly, a TEM sample 39 is defined in the wafer section 30 and separates the first cross-section void 36 from the second cross-section void 46. The focused ion beam 44 cuts the TEM sample 39 until the TEM sample 39 has a thickness which typically does not exceed about 100 nm, and which is preferably from about 10 nm to about 100 nm thick.

Upon the initial cutting of the wafer material from the wafer section 30 to define the second cross-section void 46, some metal particles are dislodged from the metal cutting line 42. Since it covers the entire sidewall 38 of the TEM sample 39, including the defect 40, the transparent coating material 41 prevents these dislodged metal particles from damaging or altering the defect 40 in the TEM sample 39.

After the second cross-section void 46 is cut in the wafer section 30, the TEM sample 39 is subjected to transmission electron microscopy, according to the knowledge of those skilled in the art. Accordingly, an electron beam (not shown) is transmitted through the TEM sample 39. An image (not shown) of the defect 40, based on such factors as the electron wavelength, accelerating voltage and thickness of the TEM sample 39, is generated on a screen (not shown) of the TEM system. The transparent coating material 41 increases the translucence of the TEM sample 39 in such a manner as to enhance the TEM-induced image of the defect 40. Semiconductor manufacturing personnel use the imaging data to fine-tune or alter the semiconductor fabrication process steps in an effort to maximize product performance and reliability, as is well-known by those skilled in the art.

While the preferred embodiments of the invention have been described above, it will be recognized and understood that various modifications can be made in the invention and the appended claims are intended to cover all such modifications which may fall within the spirit and scope of the invention.

What is claimed is:

1. A method of preparing a TEM sample, comprising the steps of:

providing a wafer section having a defect;

providing a cutting line on said wafer section adjacent to said defect;

cutting a first cross-section void in said wafer section along said cutting line to expose said defect;

depositing a substantially transparent coating material on said defect; and cutting a second cross-section void in said wafer section along said cutting line to define said TEM sample.

2. The method of claim 1 wherein said cutting line comprises a metal cutting line.

3. The method of claim 1 wherein said coating material comprises an epoxy.

4. The method of claim 3 wherein said cutting line comprises a metal cutting line.

5. The method of claim 1 wherein said TEM sample has a thickness of from about 10 nm to about 100 nm.

6. The method of claim 5 wherein said cutting line comprises a metal cutting line.

7. The method of claim 5 wherein said coating material comprises an epoxy.

8. The method of claim 7 wherein said cutting line comprises a metal cutting line.

* * * * *